United States Patent
Mickiewicz et al.

(10) Patent No.: US 8,323,294 B2
(45) Date of Patent: Dec. 4, 2012

(54) TETHER TENSIONING INSTRUMENT

(75) Inventors: Christopher Mickiewicz, Bridgewater, MA (US); Michael A. Slivka, Taunton, MA (US); Matthew Hannen, Boston, MA (US); Michael A. Fisher, Middleborough, MA (US); Hassan A. Serhan, S. Easton, MA (US); John Riley Hawkins, Cumberland, RI (US)

(73) Assignee: DePuy Spine, Inc., Raynham, MA (US)

( * ) Notice: Subject to any disclaimer, the term of this patent is extended or adjusted under 35 U.S.C. 154(b) by 1260 days.

(21) Appl. No.: 11/842,371

(22) Filed: Aug. 21, 2007

(65) Prior Publication Data

US 2009/0054902 A1    Feb. 26, 2009

(51) Int. Cl.
*A61B 17/56* (2006.01)
(52) U.S. Cl. .................. 606/103; 606/101; 606/105
(58) Field of Classification Search .............. 606/57, 606/74, 86 A, 86 B, 90, 101, 102, 103, 105, 606/263, 279, 282
See application file for complete search history.

(56) References Cited

U.S. PATENT DOCUMENTS

| | | | | |
|---|---|---|---|---|
| 3,386,437 | A * | 6/1968 | Treace | 606/105 |
| 4,252,158 | A * | 2/1981 | McDade | 140/123.6 |
| 5,058,365 | A * | 10/1991 | Kagi | 53/582 |
| 5,312,410 | A * | 5/1994 | Miller et al. | 606/86 R |
| 5,417,698 | A * | 5/1995 | Green et al. | 606/139 |
| 5,449,361 | A | 9/1995 | Preissman | |
| 5,782,831 | A | 7/1998 | Sherman et al. | |
| 5,910,141 | A * | 6/1999 | Morrison et al. | 606/86 A |
| 6,146,386 | A | 11/2000 | Blackman et al. | |
| 6,616,667 | B1 | 9/2003 | Steiger et al. | |
| 6,648,888 | B1 * | 11/2003 | Shluzas | 606/86 A |
| 6,679,889 | B1 * | 1/2004 | West et al. | 606/88 |
| 6,716,218 | B2 * | 4/2004 | Holmes et al. | 606/105 |
| 7,168,457 | B2 * | 1/2007 | Bernard | 140/123.6 |
| 7,275,336 | B2 * | 10/2007 | Casutt et al. | 33/797 |
| 7,371,239 | B2 * | 5/2008 | Dec et al. | 606/279 |
| 7,611,517 | B2 * | 11/2009 | Lim | 606/86 A |
| 7,713,274 | B2 * | 5/2010 | Shluzas et al. | 606/105 |
| 2003/0225408 | A1 * | 12/2003 | Nichols et al. | 606/61 |

(Continued)

FOREIGN PATENT DOCUMENTS

FR    2777449 A1    10/1999

OTHER PUBLICATIONS

International Search Report, PCT/US2008/071431, dated Nov. 12, 2008.

(Continued)

*Primary Examiner* — Alvin Stewart
*Assistant Examiner* — Jerry Cumberledge
(74) *Attorney, Agent, or Firm* — Nutter McClennen & Fish LLP (57) ABSTRACT

Various methods and devices are provided for tensioning a tether. In one embodiment, a tether tensioning device is provided and includes a tensioning mechanism adapted to couple to a tether extending along a path between at least two bone anchors implanted in adjacent vertebrae. The tensioning mechanism can be adapted to apply a tensioning force to the tether along the path of the tether to thereby move the tether along the path. The device further includes an actuation mechanism movably coupled to the tensioning mechanism such that the actuation mechanism is adapted to effect movement of the tensioning mechanism to control the tensioning force applied to the tether.

20 Claims, 9 Drawing Sheets

U.S. PATENT DOCUMENTS

2003/0236529 A1   12/2003  Shluzas et al.
2004/0138666 A1    7/2004  Molz et al.
2006/0009777 A1    1/2006  Lim et al.
2006/0025768 A1*  2/2006  Iott et al. .......................... 606/61
2007/0270842 A1* 11/2007  Bankoski et al. ................ 606/61
2008/0045950 A1*  2/2008  Dewey ............................ 606/61

OTHER PUBLICATIONS

Extended European Search Report issued May 4, 2012 for Application No. 08796759.2 (8 Pages).

* cited by examiner

TETHER TENSIONING INSTRUMENT

FIELD

The present application relates to devices and methods for tensioning a tether extending between bone anchors implanted in bone.

BACKGROUND

Spinal deformities, which include rotation, angulation, and/or curvature of the spine, can result from various disorders, including, for example, scoliosis (abnormal curvature in the coronal plane of the spine), kyphosis (backward curvature of the spine), and spondylolisthesis (forward displacement of a lumbar vertebra). Early techniques for correcting such deformities utilized external devices that apply force to the spine in an attempt to reposition the vertebrae. These devices, however, resulted in severe restriction and in some cases immobility of the patient. Furthermore, current external braces have limited ability to correct the deformed spine and typically only prevent progression of the deformity. Thus, to avoid this need, several rod-based techniques were developed to span across multiple vertebrae and force the vertebrae into a desired orientation.

In rod-based techniques, one or more rods are attached to the vertebrae at several fixation sites to progressively correct the spinal deformity. The rods are typically pre-curved intraoperatively to a desired adjusted spinal curvature. Wires as well as bone screws can be used to pull individual vertebra toward the rod. Once the spine has been substantially corrected, the procedure typically requires fusion of the instrumented spinal segments.

While several different rod-based systems have been developed, they tend to be cumbersome, requiring complicated surgical procedures with long operating times to achieve correction. Further, intraoperative adjustment of rod-based systems can be difficult and may result in loss of mechanical properties due to multiple bending operations. The rigidity and permanence of rigid rod-based systems can also hinder or prevent growth of the spine and they generally require fusion of many spine levels, drastically reducing the flexibility of the spine. To help remedy some of these issues, a tether and anchor system can be used to correct curvature of the spine using a number of anchors disposed within the spinal bones connected with tethers extending between them. The elasticity of the tethers prevents some of the problems with the rigidity and permanence of the rod-based systems, although the tethers must be tensioned after implantation to achieve the desired force between the anchor to correct the spinal deformities.

Accordingly, there remains a need for improved methods and devices for correcting spinal deformities and, in particular, there remains a need for methods and devices for tensioning a tether extending between anchors implanted in bone.

SUMMARY

Various methods and devices for tensioning a tether are provided. In one embodiment, a tether tensioning device is provided for tensioning a tether extending along a path between at least two bone anchors implanted in adjacent vertebrae and includes a tensioning mechanism adapted to couple to a tether seated across at least two bone anchors. The tensioning mechanism can be adapted to apply a tensioning force to the tether along the path of the tether to move the tether along the path. The device can also include an actuation mechanism movably coupled to the tensioning mechanism such that the actuation mechanism is adapted to effect movement of the tensioning mechanism to control the tensioning force applied to the tether. The tensioning mechanism and the actuation mechanism can be movably coupled to an elongate shaft. In an exemplary embodiment, the path can be a substantially straight path.

The tether tensioning mechanism can have a variety of configurations, but in one embodiment the tensioning mechanism can include a wheel rotatably coupled to a distal end of the elongate shaft and adapted to rotate to apply a tensioning force to a tether. The actuation mechanism can include a shaft having a pawl adapted to engage a plurality of teeth formed on the wheel to rotate the wheel. The device can further include a stationary handle coupled to a proximal end of the elongate shaft, and an actuator coupled to the stationary handle and adapted to pivot toward the stationary handle to move the shaft to cause the wheel to rotate. The device can also include a grasping member movably coupled to the elongate shaft and adapted to grasp a tether between the grasping member and the wheel, and optionally a locking mechanism formed on the elongate shaft and adapted to lock the wheel in a fixed position to lock the tether between the grasping member and the wheel.

In another embodiment, the tensioning mechanism can be in the form of a lever arm slidably coupled to the elongate shaft and adapted to slide to apply a tensioning force to a tether. The actuation mechanism can include a pusher movably coupled to the elongate shaft and adapted to apply a force to the lever arm to cause the lever arm to slide. A cam surface can be formed on the elongate shaft and it can be positioned to cam the lever arm away from the elongate shaft during sliding movement of the lever arm. The device can also include a grasping member for coupling the lever arm to a tether and it can be adapted to grasp a tether to anchor the tether during tensioning. For example, at least one surface feature can be formed on a distal end of the lever arm and it can be adapted to engage a tether.

Spinal anchoring and tensioning systems are also provided, and in one embodiment the system can include first and second bone anchors having a receiver member and a bone-engaging member, and a tether adapted to extend along a path between the receiver members of the first and second bone anchors. A tether tensioning device can be adapted to be positioned adjacent to the receiver member of at least one of the first and second bone anchors and to engage the tether such that the tether tensioning device is effective to apply a tensioning force to the tether along the path to move the tether along the path of the tether. The tether tensioning device can have a variety of configurations, including a wheel adapted to rotate to move the tether along the path, and a lever arm adapted to slide and pivot to move the tether along the path. The tether tensioning device can also include a lumen formed therethrough and adapted to receive a driver for applying a locking mechanism to the receiver member.

Methods for applying tension to a tether are also provided, and in one embodiment the method can include grasping a tether extending along a path between first and second bone anchors implanted in adjacent vertebrae, and actuating a tensioning mechanism to apply a tensioning force to the tether along the path of the tether. The path of the tether can be a substantially straight line extending across the first and second bone anchors. The tensioning mechanism can be formed on a tensioning device that is positioned adjacent to one of the first and second bone anchors. The method can also include inserting a driver through a shaft of the tensioning device, and manipulating the driver to lock a locking mechanism to the bone anchor to thereby lock the tether in a fixed position relative to the bone anchor. In one embodiment, grasping the tether can include grasping the tether between the tensioning mechanism and a grasping member adapted to grip the tether and anchor the tether in place.

The tensioning mechanism can have a variety of configuration. In one embodiment, the tensioning mechanism can include a wheel, and the wheel can be rotated to apply a tensioning force to the tether. For example, the wheel can be rotated by moving a trigger operatively associated with the wheel. The trigger can be coupled to a shaft and a pawl that rotates the wheel when the trigger is moved. In another embodiment, the tensioning mechanism can include a lever arm slidably and pivotally coupled to a shaft of a tensioning device. Actuating the tensioning mechanism can include sliding and pivoting the lever arm relative to the shaft to push the grasping mechanism along the path of the tether to thereby apply tension to the tether. Applying a tensioning force to the tether can include actuating a pusher movably coupled to the shaft to slide the lever arm relative to the shaft such that the lever arm applies tension to the tether. Grasping the tether can include grasping the tether with a grasping mechanism positioned adjacent to the tensioning mechanism such that movement of the tensioning mechanism is effective to move the grasping mechanism to thereby apply tension to the tether.

BRIEF DESCRIPTION OF THE DRAWINGS

Various exemplary embodiments disclosed herein will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope is defined solely by the claims. The features illustrated or described in connection with one exemplary embodiment may be combined with the features of other embodiments. Such modifications and variations are intended to be included within the scope.

Various exemplary methods and devices are provided for tensioning a tether extending across one or more anchors implanted in bone. In one embodiment, a tensioning mechanism is provided that is adapted to couple to a tether extending along a path between one or more bone anchors implanted in adjacent vertebrae. The tensioning mechanism can be adapted to apply a tensioning force to the tether along the path of the tether as it extends across the bone anchor(s). The path can be, for example, a path extending along and substantially parallel to a patient's spinal column. The path can, however, have slight departures out of a linear line due to natural curvatures in the spinal column. The path can also be substantially perpendicular to an axis of the device, such that the tensioning mechanism applies tension in a direction perpendicular to an axis of the device. The tensioning mechanism can include an actuation mechanism movably coupled thereto and adapted to effect movement of the tensioning mechanism to control the tensioning force applied to the tether.

Figure 1:
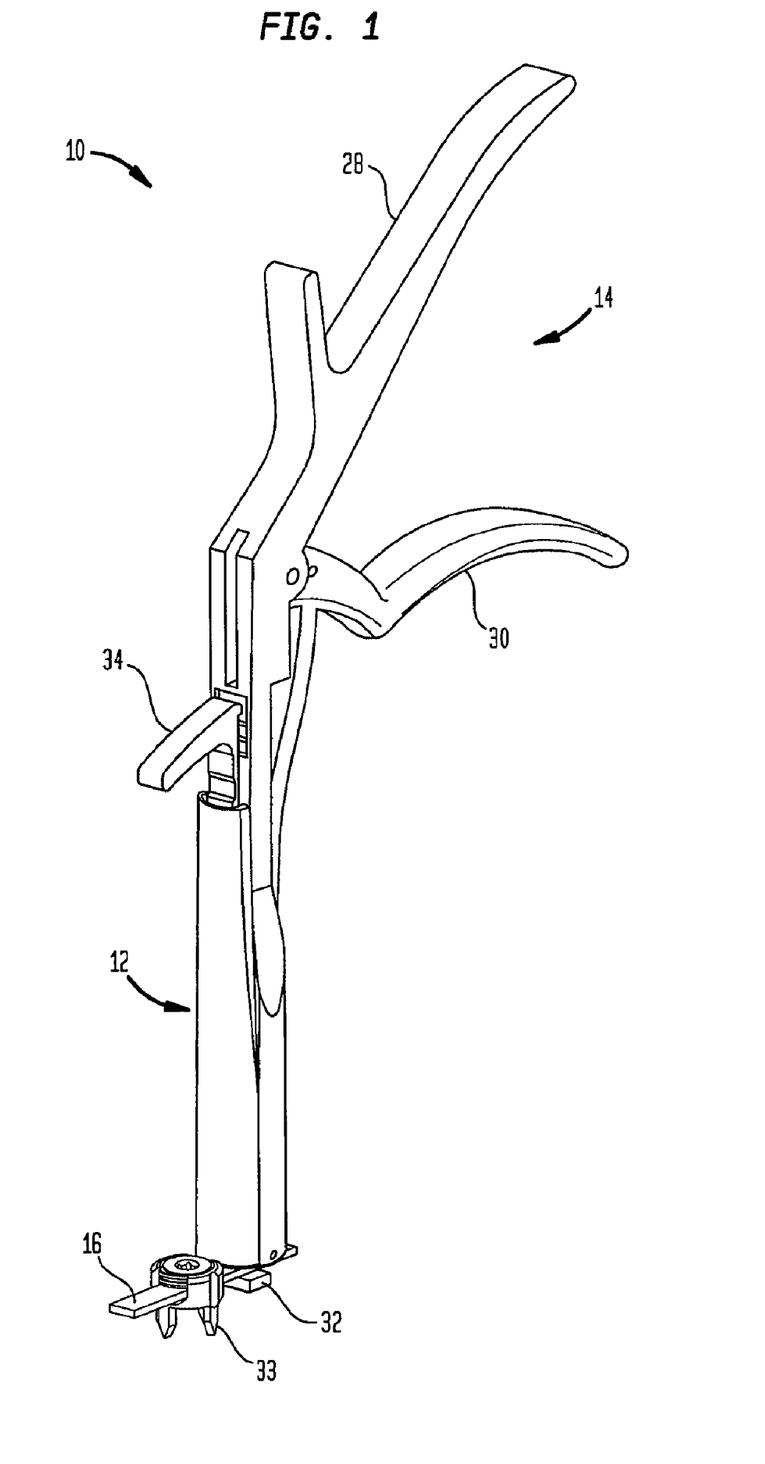
FIG. 1 is a perspective view of one embodiment of a tether tensioning device shown engaging a tether extending through a bone anchor.
Figure 2:
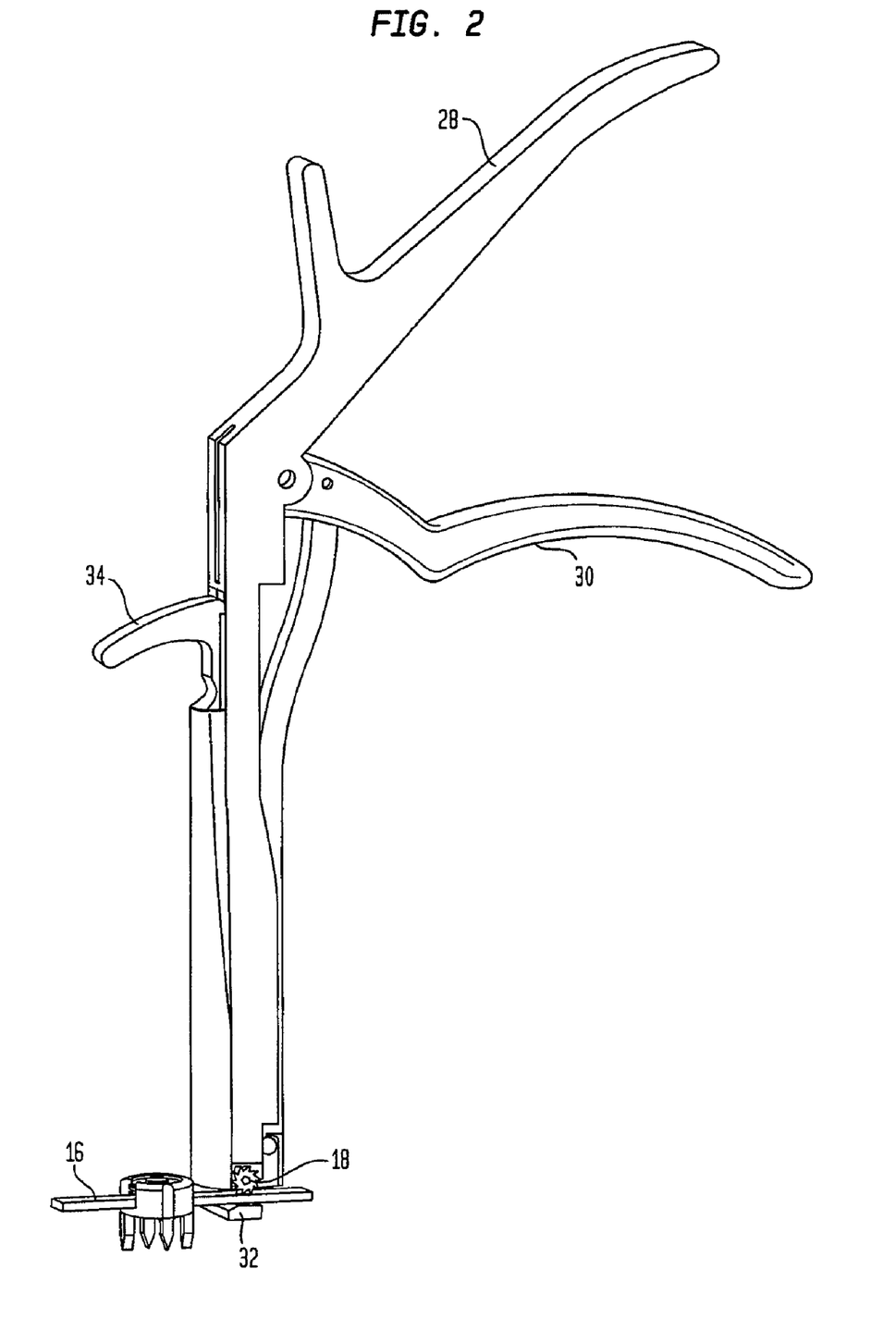
FIG. 2 is a side view of the tether tensioning device of FIG. 1 showing a tensioning mechanism including a wheel and ratchet adapted to tension a tether along its path.

FIGS. 1-2 illustrate one exemplary embodiment of a tether tensioning device 10 that generally includes an elongate shaft 12 extending from a handle 14. A tensioning mechanism in the form of a rotatable wheel 18 and an actuation mechanism in the form of a pawl 24 are coupled to the elongate shaft 12. The rotatable wheel 18 can be adapted to engage a tether 16 seated across one or more bone anchors implanted in bone, and the pawl 24 can be adapted to move relative to the elongate shaft 12 and the wheel 18 to effect movement of the rotatable wheel 18 to control a tensioning force applied to the tether 16 by the rotatable wheel 18.

The elongate shaft 12 can have a variety of configurations, and it can be flexible or rigid depending on the intended use. In an exemplary embodiment, the elongate shaft 12 has a length that allows the distal end of the elongate shaft 12 to be positioned adjacent to a tether extending along a spinal column, while the proximal end remains external to the body. This length allows the elongate shaft 12 to extend from the tissue surface to the treatment site, e.g., to a bone anchor implanted in a vertebra. A person skilled in the art will appreciate that the elongate shaft 12 can be made from a variety of biocompatible materials that have properties sufficient to enable the elongate shaft 12 to be inserted into the body.

Figure 3:
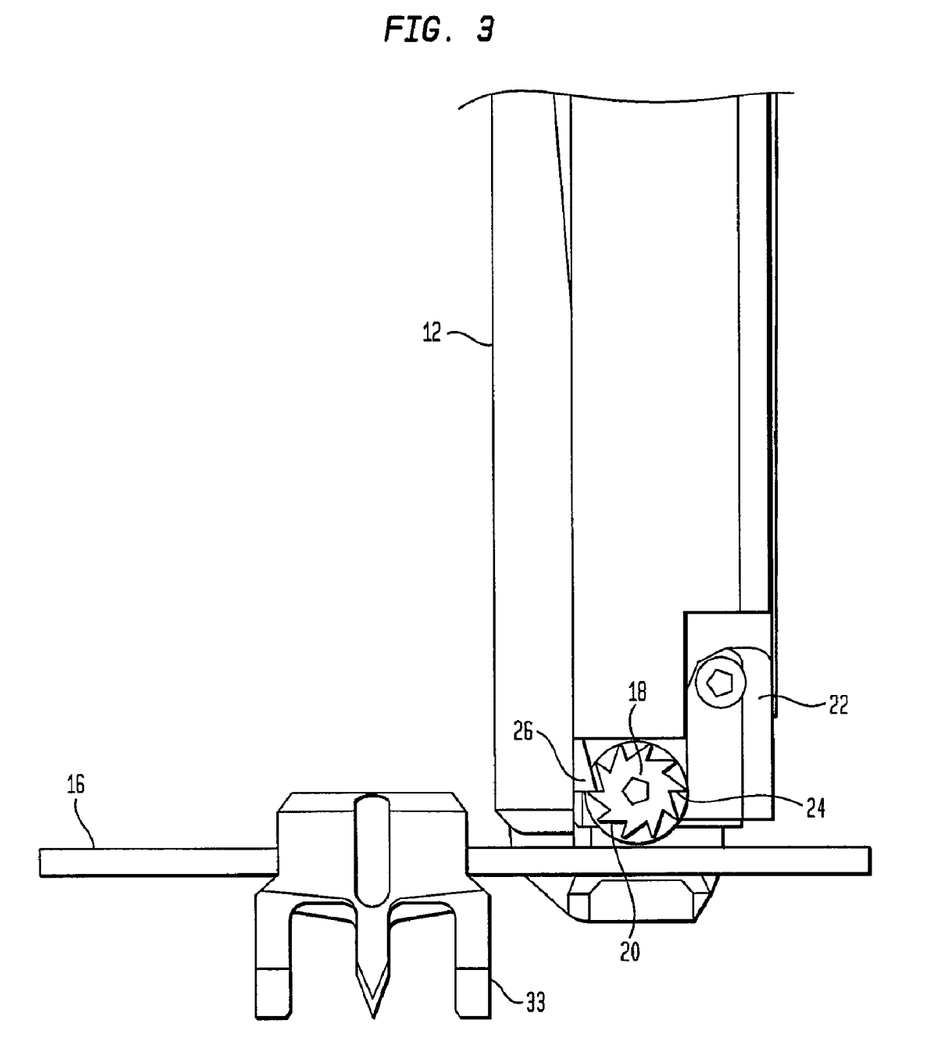
FIG. 3 is a side view of the tensioning mechanism of FIG. 2.
Figure 4:
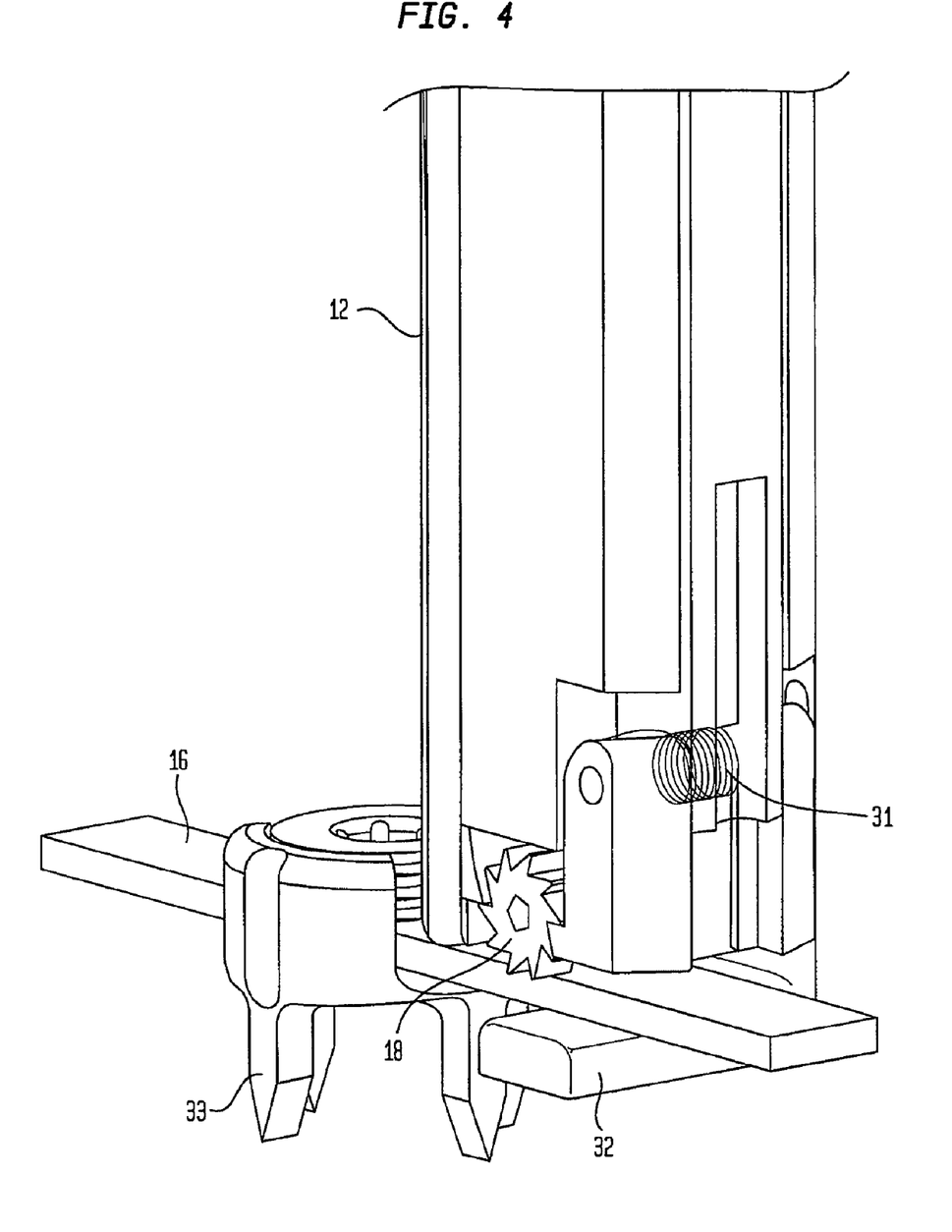
FIG. 4 is a perspective view of the tensioning mechanism of FIG. 2.
Figure 5:
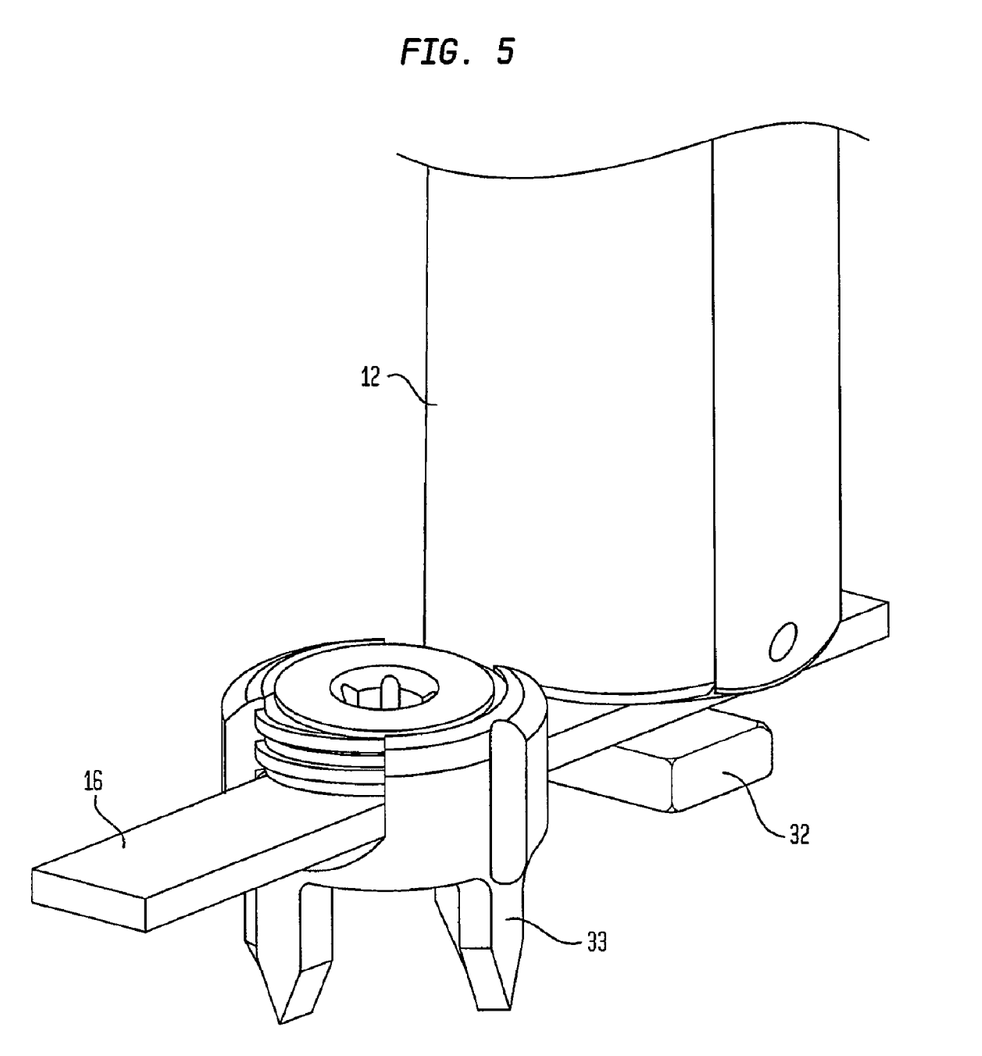
FIG. 5 is a perspective view of a grasping member engaging a tether during tensioning of the tether tensioning device of FIG. 1.

As indicated above, the tensioning mechanism can be in the form of a wheel 18, shown in more detail in FIGS. 3-4, that is rotatably coupled to a distal end of the elongate shaft 12 and that is adapted to rotate to apply a tensioning force to the tether 16. The wheel 18 can be positioned at a distal end of the elongate shaft 12 in a variety of ways. In the illustrated embodiment, the wheel 18 is housed in a recess formed in the distal end of the elongate shaft 12. However, in order for the wheel 18 to engage the tether 16 to apply a tensioning force thereto, a distal portion of the wheel 18 can extend distally beyond the distal-most end of the elongate shaft 12. A person skilled in the art will appreciate that the wheel 18 can be positioned relative to the elongate shaft 12 in any way that allows a portion of the wheel 18 to engage the tether 16. In addition, the wheel 18 can be coupled to the elongate shaft 12 in a variety of ways. For example, a pivot pin can extend through the wheel 18 and mate to the elongate shaft 12 to allow the wheel 18 to rotate relative to the elongate shaft 12. A person skilled in the art will appreciate, however, that various other techniques can be used to rotatably couple the wheel 18 and the elongate shaft 12. The wheel 18 can also include features formed thereon for engaging the tether 16. For example, the wheel 18 can include a plurality of teeth 20 configured to engage the tether 16. The teeth 20 can have various shapes and sizes, for example the teeth 20 can be angled to facilitate engagement of the tether 16 as the wheel 18 is rotated.

As indicated above, the device 10 can also include an actuation mechanism that is adapted to effect movement of the rotatable wheel 18 to control a tensioning force applied to the tether 16. In the illustrated embodiment, the actuation mechanism is in the form of a pawl 24 that is movably coupled to a pusher 22. The pusher 22 is located along a portion of the elongate shaft 12. For example, it can be located within a longitudinal recess formed along the length of the elongate shaft 12 extending from an actuator adapted to move the pusher 22 to a distal end of the elongate shaft 12. A person skilled in the art will appreciate that the pusher 22 can be coupled to the elongate shaft 12 in a variety of ways, including movably coupled to an outside portion of the elongate shaft 12, or being housed in a lumen formed through the elongate shaft 12. The pusher 22 can also have a variety of configurations. In an exemplary embodiment, the pusher 22 has a length that allows the distal end of the pusher 22 to mate to the pawl 24, while the proximal end of the pusher 22 is coupled to an actuator, as will be discussed in more detail below. The actuator can be adapted to move the pusher 22 in a longitudinal direction along the elongate shaft 12 between a distal position and a proximal position to cause the pawl 24 to effect rotation of the wheel 18. As indicated above, the distal end of the pusher 22 can be mated to the pawl 24. In an exemplary embodiment, the pusher 22 is pivotally mated to the pawl 24 to allow the pawl 24 to move into and out of engagement with the wheel 18.

The device can also optionally include a biasing element, such as a spring 31, positioned within the shaft 12 and abutting against the pawl 24. When the pusher 22 is in the distal position, the spring 31 can bias the pawl 24 into engagement with a tooth 20 formed on the wheel 18. As the pusher 22 is moved into the proximal position using the actuator, the pawl 24 will pull the engaged tooth 20 on the wheel 18 in a proximal direction, thereby rotating the wheel 18. This rotation of the wheel 18 causes a tensioning force to be applied to the tether 16 along its path to tension the tether 16 relative to at least one bone anchor 33 implanted in the spine. When the pusher 22 is returned to the distal position, the pawl 24 will pivot out of engagement with the teeth 20, thereby compressing the spring 31. This allows the pawl 24 to slide over the teeth 20 of the wheel 18 and into engagement with an adjacent tooth 20. The pusher 22 can then be moved proximally once again to rotate the wheel 18 to apply additional tension to the tether. A person skilled in the art will appreciate that any components adapted to rotate the wheel to tension the tether can be used in place of the actuation mechanism described above. For example, a cable can be wound around the wheel and pulling on the cable can be effective to rotate the wheel 18 to apply a tensioning force to the tether 16.

In order to facilitate engagement of the tether 16 by the wheel 18, the distal end of the elongate shaft 12 can include a grasping member 32 disposed thereon and adapted to grasp the tether 16 between the grasping member 32 and the wheel 18. The grasping member 32 can have any size and shape to facilitate grasping of the tether 16, but in the embodiment shown in FIGS. 1-5, it is in the form of an elongate foot extending from the distal end of the elongate shaft 12 and positioned substantially transverse, e.g., perpendicular, to the elongate shaft 12 and a distance from the wheel 18 sufficient to allow the tether 16 to slide between the grasping member 32 and the wheel 18. The grasping member 32 can also be movable between a first position in which the tether 16 is not engaged between the grasping member 32 and the wheel, and a second position in which the tether 16 is engaged between the grasping member 32 and the wheel. The grasping member 32 can be coupled to or formed on a moveable shaft (not shown) that is disposed along or within a lumen formed in the elongate shaft 12. A proximal end of the movable shaft can be coupled to a grasping actuator 34 that can be adapted to effect vertical movement of the grasping member 32 to allow the grasping member 32 to grasp the tether 16 with the wheel 18. For example, the grasping actuator 34 can move the grasping member 32 between a first unlocked position in which the grasping member 32 is located a distance distally from the wheel 18 to allow the tether 16 to slide between the grasping member 32 and the wheel 18, and a second locked position in which the grasping member 32 is moved proximally towards the wheel 18 to allow the grasping member 32 to grasp the tether 16 therebetween.

The tensioning mechanism can also include features to prevent the wheel from back-spinning as tension is being applied. In one embodiment, the tensioning mechanism can include a locking mechanism 26 disposed on a distal end of the elongate shaft 12. The locking mechanism 26 can be sized to extend between two adjacent teeth 20 formed on the wheel 18, and it can be shaped to allow the wheel 18 to spin in one direction to apply a tensioning force to the tether 16, while preventing the wheel 18 from spinning in the opposite direction to maintain the tensioning force applied to the tether 16. For example, the locking mechanism 26 can be a triangular member having a first side coupled to the elongate shaft 12, a second side having an angle that corresponds to the angle between the two adjacent teeth 20, and a third side substantially perpendicular to the first side that is effective to block rotation of the teeth in one direction. A person skilled in the art will appreciate that any mechanism can be used in conjunction with the wheel 18 that can prevent back-spinning of the wheel during the application of tension to the tether 16.

As previously discussed, the elongate shaft 12 extends from the handle 14 which can have any shape and size, but is preferably adapted to facilitate grasping and manipulation of the device 10. In the illustrated embodiment, as shown in FIGS. 1-2, the handle 14 includes a stationary member 28 and a actuator 30 pivotally coupled to the stationary member 28. As discussed above, a distal end of the actuator 30 can be coupled to a proximal end of the pusher 22. The actuator 30 can be adapted to pivot toward the stationary member 28 to pull the pusher 22 in a proximal direction to cause the wheel 18 to rotate and apply a tensioning force to the tether 16. A person skilled in the art that any mechanism can be used to move the pusher 22 along the elongate shaft 12. Moreover, a person skilled in the art will appreciate that either of the stationary member 28 or the actuator 30 can be movable, or both of the stationary member 28 and the actuator 30 can be movable.

FIGS. 6-10 illustrate another embodiment of a device for applying tension to a tether extending across anchors implanted in bone. The device 100 is similar in configuration to device 10 described above, and has an elongate shaft 112 extending from a handle 114 and having a tensioning mechanism and an actuation mechanism coupled thereto. In the embodiment shown in FIGS. 6-10, the tensioning mechanism includes a lever arm 118 that is slidably coupled to a distal portion of the elongate shaft 112 and that is adapted to slide to apply a tensioning force to a tether 116 along the path of the tether 116.

The lever arm 118 can have a variety of configurations, but in one embodiment as shown in FIGS. 6-9, it has a substantially hemi-cylindrical shape to allow the lever arm 118 to be received around a portion of the shaft 112. The lever arm 118 can be coupled to the elongate shaft 112 in a variety of ways. In the illustrated embodiment, the lever arm 118 is pivotally and slidably coupled to a distal portion of the elongate shaft 112 to allow the lever arm 118 to move distally and outwardly relative to the shaft 112. In particular, the proximal end 118a of the lever arm 118 can include pins (only one pin 118p is shown) formed on an opposed inner surfaces thereof that extend into corresponding cam recesses (only one recess 120 is shown) formed in opposed sides of the elongate shaft 112. The cam recesses 120 can be in the form of shaped slots that receive the pins and guide the pins along the cam recesses 120 to guide movement of the lever arm 118. For example, the cam recesses 120 can be adapted to guide movement of the lever arm 118 in a distal and outward direction relative to the elongate shaft 112. This allows the distal end 118b of the lever arm 118 to slide substantially parallel along the path of the tether 116 to tension the tether 116 along its path. Various techniques for moving the lever arm 118 in such a way as to apply the tensioning force along the path of the tether 116 will be discussed in more detail below.

In order to further facilitate movement of the lever arm 118 outwardly away from the elongate shaft 112, the distal end 112b of the elongate shaft 112 can include a cam surface 113 formed thereon. In particular, as shown in FIGS. 6-9, the distal end 112b of the elongate shaft 112 can include opposed arms extending outward from the longitudinal axis of the shaft 112 such that each arm defines the cam surface 113 on the top portion thereof. The cam surface 113 can slope downwardly, and the lever arm 118 can include a corresponding downwardly sloping surface 119 formed thereon that abuts against the cam surface 113. As a result, when the lever arm 118 is moved distally, the surface 119 on the lever arm 118 will abut against the cam surface 113 on the shaft 112. The cam surface 113 will thus force the distal end 118b of the lever arm 118 to move outwardly away from the distal end 112b of the elongate shaft 112, thereby allowing the lever arm 118 to move a tether along its path.

Figure 8:
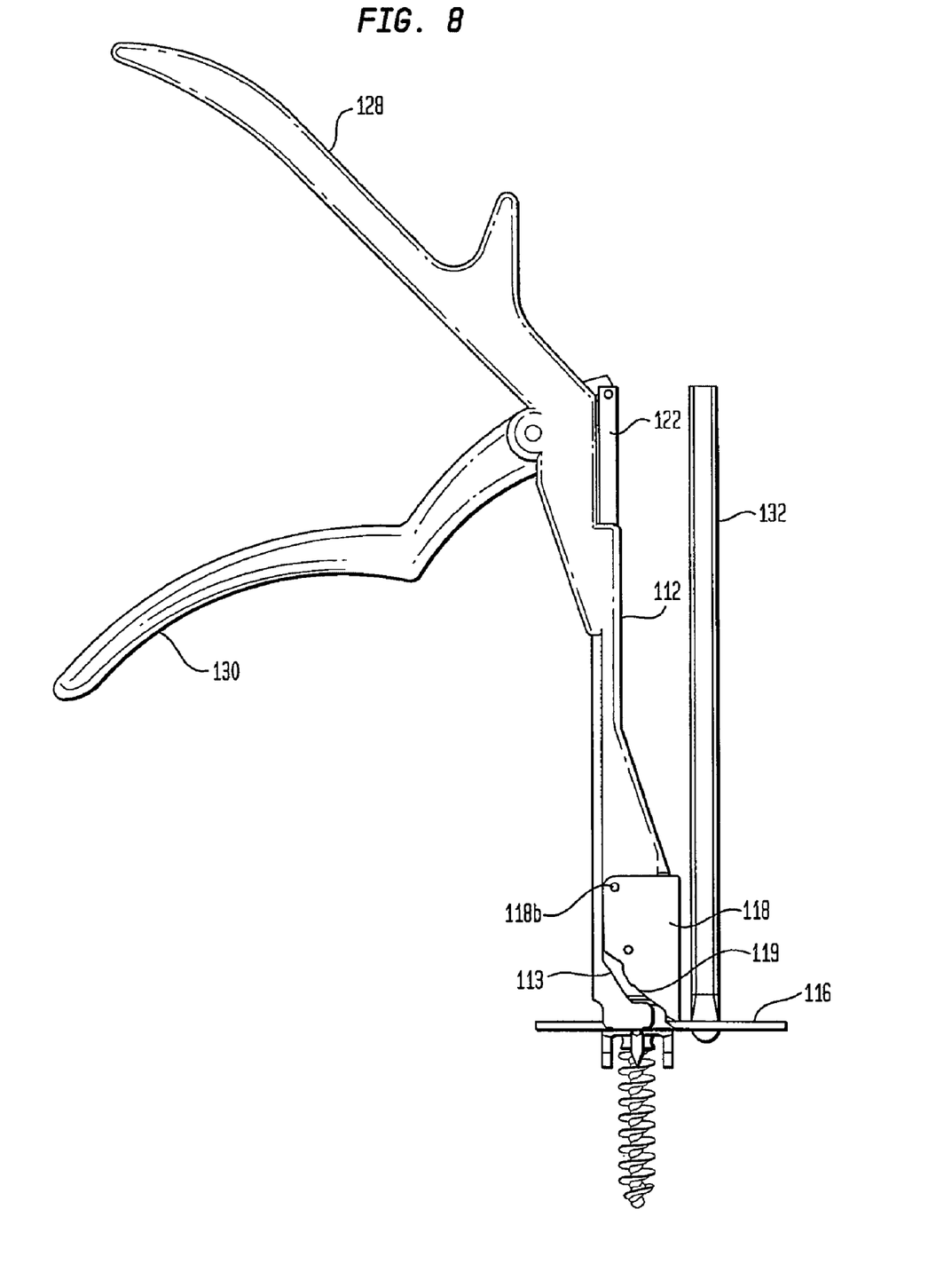
FIG. 8 is a side view of the tether tensioning device of FIG. 6 coupled to a bone anchor.
Figure 9:
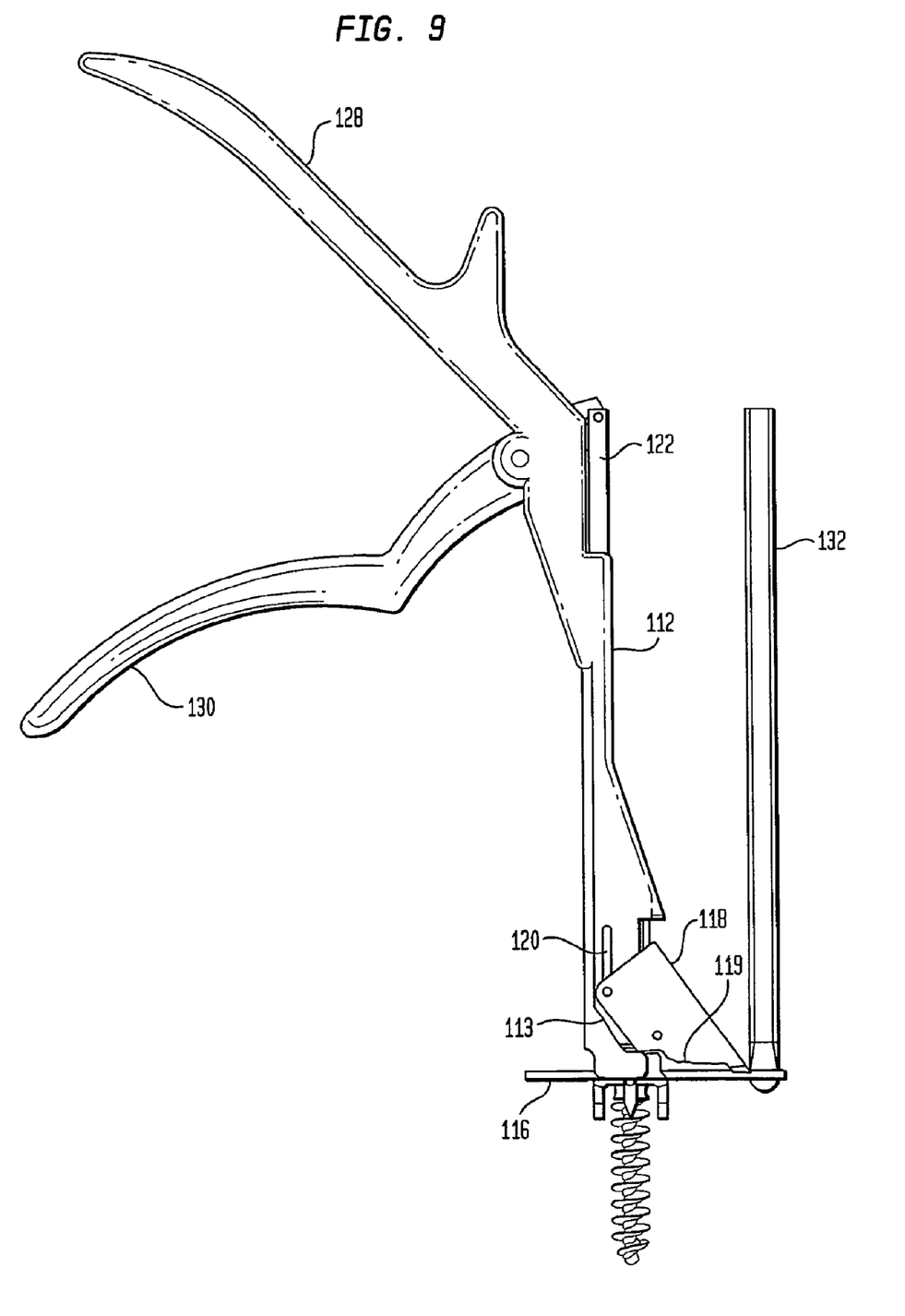
FIG. 9 is a side view of the tether tensioning device of FIG. 6 coupled to a bone anchor and showing a grasping member engaging a tether during tensioning.

In order to engage a tether to move the tether 116 along its path, the lever arm 118 can also include one or more surface features or other engagement mechanisms on the distal end 118b thereof. For example, the distal end 118b of the lever arm 118 can include one or more protrusions or teeth formed thereon and adapted to pierce a portion of the tether 116 to temporarily couple the lever arm 118 to the tether 116 to anchor the tether 116 during tensioning. Alternatively or in addition, the tether 116 could have a surface featured formed thereon, such as a raised button, to form a surface for the lever arm 118 to push against to apply a tensioning force to the tether 116. In another embodiment, a grasping member 132, shown in FIG. 8, can be positioned at a location adjacent to a bone anchor through which the tether 116 extends and can be used to grasp the tether 116 to anchor it during tensioning. In particular, FIG. 8 illustrates the grasping member 132 engaging the tether 116 adjacent to the lever arm 118. This will allow the lever arm 118 to push against the grasping member 132, and thereby move the tether 116. A person skilled in the art will appreciate that any technique or device known in the art can be used to facilitate anchoring of the tether 116 during application of the tensioning force.

In order to apply a tensioning force to the tether 116, the lever arm 118 can be actuated using an actuation mechanism. In the illustrated embodiment, the actuation mechanism is in the form of a pusher 122 that is movably coupled to the elongate shaft 112 to apply a force to the lever arm 118 to cause the lever arm 118 to slide and apply the tensioning force to the tether 116. The pusher 122 can have a variety of configuration, but in an exemplary embodiment the pusher 112 is in the form of an elongate member that extends along or through a portion of the elongate shaft 112 and that includes a distal end (not shown) that is pivotally mated to the proximal end 118a of the lever arm 118, and a proximal end 122a that is mated to an actuator 130, which will be discussed in more detail below. Actuation of the actuator 130 can be effective to cause the pusher 122 to move longitudinally along the shaft 112 to a distal position in which the pusher 122 pushes against the lever arm 118, causing the lever arm 118 to slide distally and outward to apply a tensioning force to the tether 116.

Figure 6:
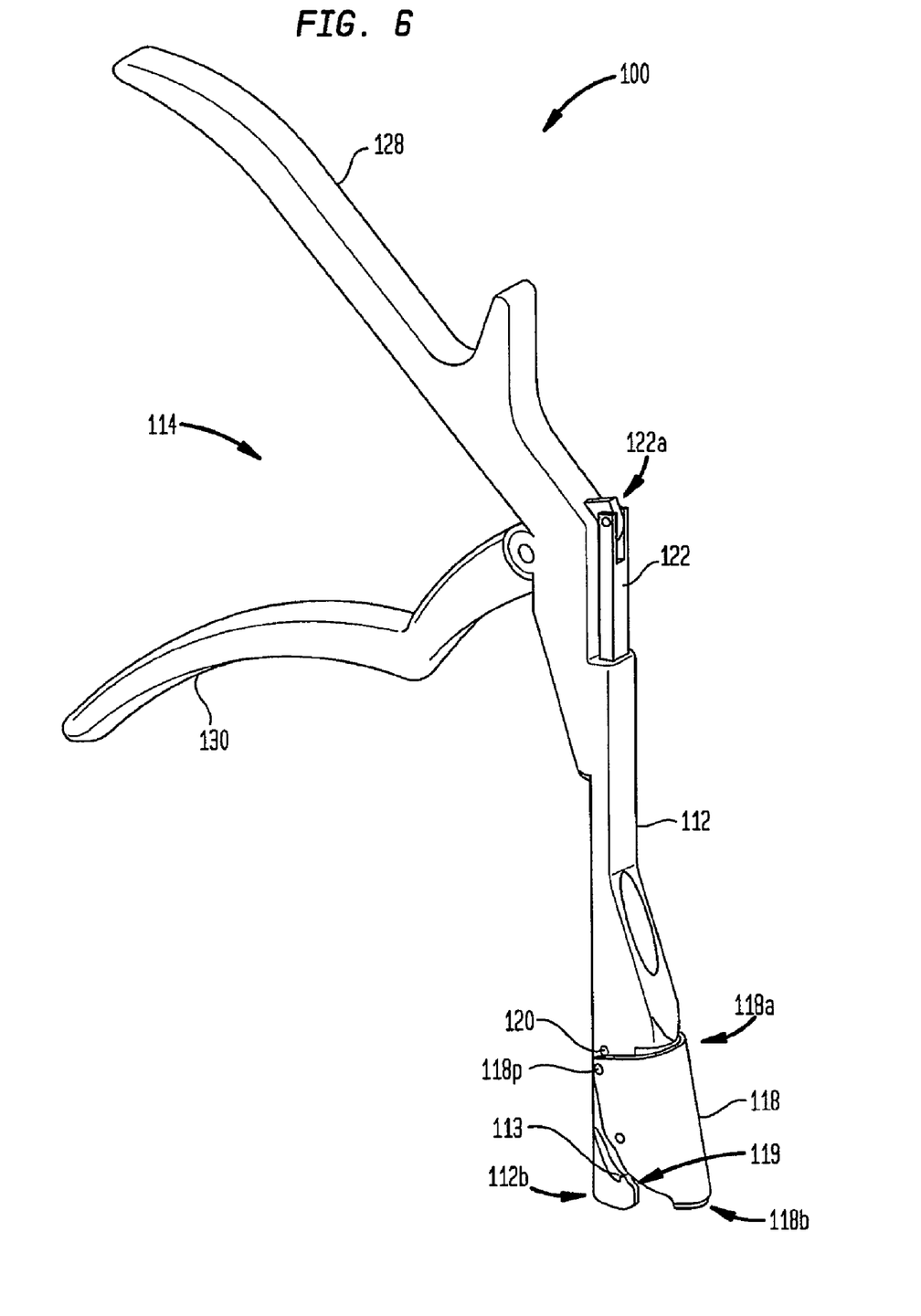
FIG. 6 is a perspective view of another embodiment of a tether tensioning device having a tensioning mechanism including a lever arm and pusher adapted to tension a tether along its path.
Figure 7:
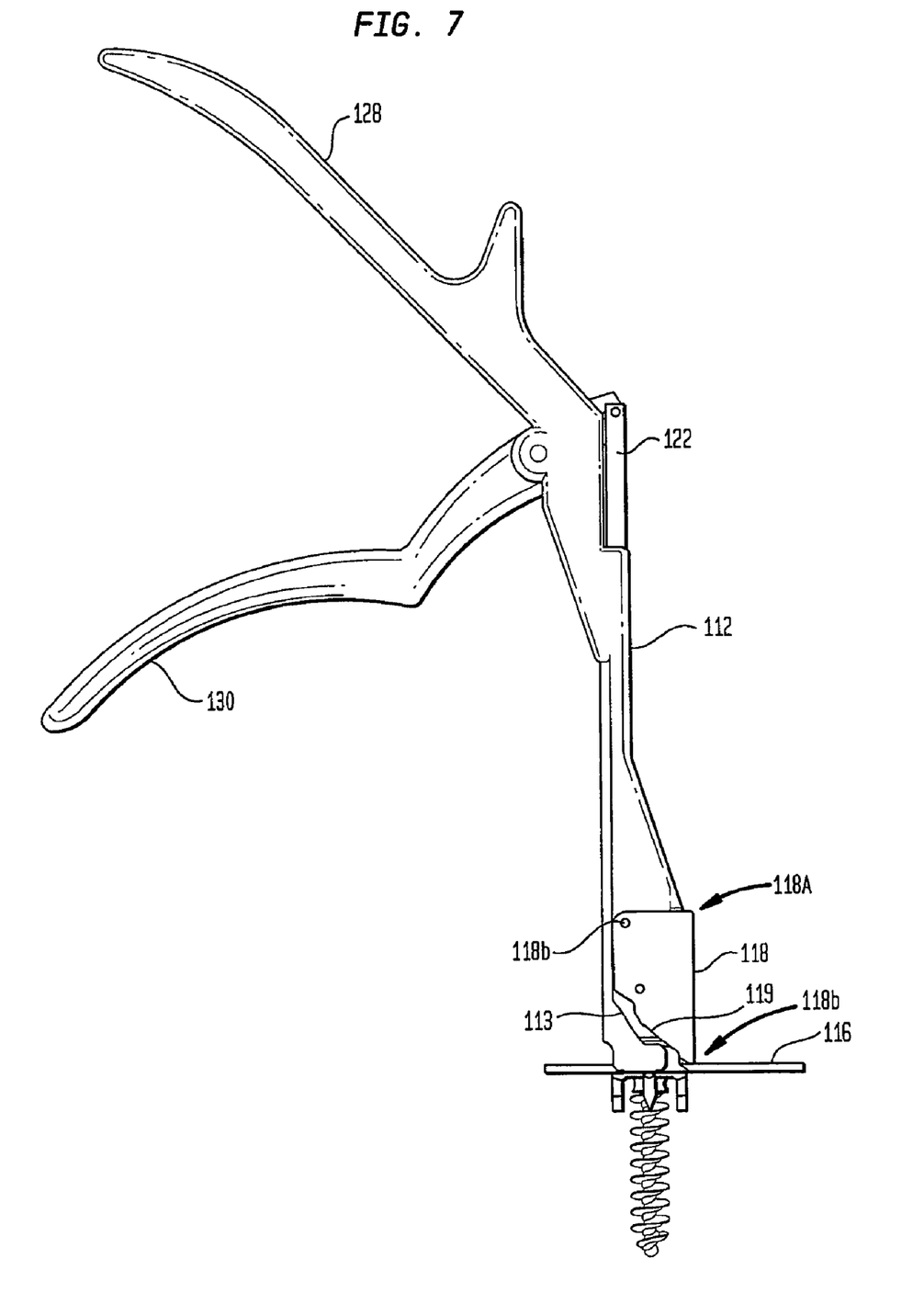
FIG. 7 is a side view of the tether tensioning device of FIG. 6 coupled to a bone anchor having a tether extending therethrough.

The pusher 122 can be moved using an actuator 130 coupled to the elongate shaft 112. In the illustrated embodiment, the actuator 130 is part of a handle assembly 114 formed on the proximal end 112 of the shaft. The handle assembly 114 can have any shape and size, but it is preferably adapted to facilitate grasping and manipulation of the device 100. In the illustrated embodiment, as shown in FIGS. 6-7, the handle assembly 114 includes a stationary portion 128 formed on and extending proximally from the elongate shaft 112 for a user to hold the handle of the device 100, and the actuator 130 which is coupled to the stationary portion 128 and is adapted to allow a user to control the tensioning of the tether 116. In an exemplary embodiment, the actuator 130 is pivotally coupled to the stationary portion 128 and to the proximal en 112a of the pusher 122. Pivotal movement of the actuator 130 toward the stationary portion 128 can be effective to move the pusher 122 in a distal direction to cause the lever arm 118 to move and slide along the tether 116 to apply a tensioning force thereto. A person skilled in the art that any mechanism can be used to move the pusher 122 to apply tensioning force to the tether 116.

Various exemplary methods for tensioning a tether are also provided. While the methods are described in connection with devices 10 and 100, a person skilled in the art will appreciate that any device can be used. In an exemplary embodiment, the device 10, 100 can be inserted through tissue, or through an access port disposed in tissue, so that the handle can extend from the tissue or port on the outside, and the distal end of the device 10, 100 can be positioned adjacent to a bone anchor. The device 10, 100 can be positioned adjacent to a tether 16, 116 extending between bone anchors to be tensioning. For example, the device 10, 100 can be removably mated directly to the bone anchor, or it can be positioned against a side of the bone anchor, or spaced apart from the bone anchor. The tether 16, 116 can be grasped to anchor the tether in place during tensioning, such as with the grasping member 32, 132 of FIG. 2 or FIG. 7. Once the tether 16, 116 is anchored in place, a force can be applied to the actuator 30, 130 of device 10, 100 to move it toward the stationary member 28, 128 and thereby cause a tensioning force to be applied to the tether 16, 116. For example, the wheel 18 of device 10 will rotate to push or pull the tether 16 away from the anchor to apply the tensioning force thereto. With device 100, the lever arm 118 will slide to push the tether 116 away from the anchor to apply the tensioning force thereto. In an exemplary embodiment, the tether 16, 116 is tensioned along its path as it extends longitudinally along the spinal column. This applies the tension in such as a way as to push or pull on the tether 16, 116 without substantially bending the tether 16, 116. The proper tension can be applied to the tether 16, 116, and after the tether 16, 116 has been locked in the bone anchor to retain the tension thereon, the device 10, 100 can be removed and the tether 16, 116 can be released from the grasping member 32, 132. In one embodiment, the tether can be locked between adjacent bone anchors by applying a locking mechanism, such as a set screw, to each bone anchor. A person skilled in the art will appreciate that any mechanism can be used to lock the tensioned tether 16, 116 between adjacent bone anchors.

A person skilled in the art will appreciate that the various methods and devices disclosed herein can be formed from a variety of materials. Moreover, particular components can be implantable and in such embodiments the components can be formed from various biocompatible materials known in the art. Exemplary biocompatible materials include, by way of non-limiting example, composite plastic materials, biocompatible metals and alloys such as stainless steel, titanium, titanium alloys and cobalt-chromium alloys, and any other material that is biologically compatible and non-toxic to the human body.

One skilled in the art will appreciate further features and advantages based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. A tether tensioning device, comprising:
an elongate shaft having proximal and distal ends;
a tensioning mechanism positioned at the distal end of the elongate shaft, the tensioning mechanism being adapted to couple to a tether extending along a longitudinal axis between at least two bone anchors implanted in adjacent vertebrae, and the tensioning mechanism being adapted to apply a tensioning force to the tether along the longitudinal axis of the tether;
a pusher shaft extending longitudinally along and being slidable in a longitudinal direction relative to the elongate shaft;
a pivotable actuator positioned at the proximal end of the elongate shaft and configured to move the pusher shaft longitudinally; and
an actuation mechanism movably coupled to a distal end of the pusher shaft and to the tensioning mechanism such that the actuation mechanism is adapted to effect movement of the tensioning mechanism to control the tensioning force applied to the tether.

2. The device of claim 1, wherein the tensioning mechanism and the actuation mechanism are movably coupled to the elongate shaft.

3. The device of claim 2, wherein the tensioning mechanism is adapted to apply the tensioning force in a direction perpendicular to a longitudinal axis of the elongate shaft.

4. The device of claim 1, wherein the tensioning mechanism comprises a wheel rotatably coupled to the distal end of the elongate shaft and adapted to rotate to apply the tensioning force to the tether.

5. The device of claim 1, wherein the actuation mechanism comprises a pawl adapted to engage a plurality of teeth formed on the tensioning mechanism to rotate the tensioning mechanism.

6. The device of claim 5, wherein rotation of the tensioning mechanism is effective to apply the tensioning force.

7. The device of claim 5, further comprising a biasing element that biases the pawl into engagement with the plurality of teeth.

8. The device of claim 1, further comprising a grasping member positioned adjacent to the tensioning mechanism and adapted to grasp a tether between the grasping member and the tensioning mechanism.

9. The device of claim 8, further comprising a locking mechanism operatively associated with the tensioning mechanism and adapted to lock the tensioning mechanism in a fixed position to lock a tether between the grasping member and the tensioning mechanism.

10. The device of claim 9, wherein the locking mechanism is configured to directly contact the tensioning mechanism to lock the tensioning mechanism.

11. The device of claim 8, wherein the grasping member is configured to move between an unlocked position in which the grasping member is positioned distal of the tensioning mechanism and a locked position in which the grasping member is moved proximally toward the tensioning mechanism.

12. The device of claim 1, wherein the tensioning mechanism comprises a rotatable wheel that is configured to rotate to apply the tensioning force to the longitudinal axis of the tether.

13. A tensioning device, comprising:
an elongate shaft having a proximal end and a distal end;
a rotatable wheel disposed on the distal end of the elongate shaft; and
a grasping arm positioned distal to the rotatable wheel, the grasping arm being longitudinally movable proximally toward and distally away from the rotatable wheel;
wherein the rotatable wheel and the grasping arm are configured to engage a tether therebetween such that rotation of the wheel is effective to move the tether in a direction substantially perpendicular to a longitudinal axis of the elongate shaft.

14. The device of claim 13, further comprising a pawl disposed on the distal end of the elongate shaft and configured to rotate the wheel.

15. The device of claim 14, further comprising a pusher shaft movably coupled to the pawl and configured to move longitudinally along the elongate shaft to cause the pawl to rotate the wheel.

16. The device of claim 15, wherein the pusher shaft extends longitudinally along a recess formed in the elongate shaft.

17. The device of claim 15, wherein the pusher shaft is configured to move proximally along the elongate shaft to cause the pawl to rotate the wheel.

18. The device of claim 17, wherein a proximal end of the pusher shaft is coupled to a pivotable actuator, and movement of the pivotable actuator causes the pusher shaft to move proximally along the elongate shaft.

19. The device of claim 14, wherein the pawl is biased into engagement with the rotatable wheel.

20. The device of claim 13, wherein the rotatable wheel further comprises a plurality of teeth for engaging the tether.

* * * * *